United States Patent [19]

Granger et al.

[11] Patent Number: 5,123,911
[45] Date of Patent: Jun. 23, 1992

[54] METHOD FOR ATTACHING A SURGICAL NEEDLE TO A SUTURE

[75] Inventors: Richard N. Granger, Huntington; Michael S. Kassim, Monroe, both of Conn.

[73] Assignee: United States Surgical Corporation, Norwalk, Conn.

[21] Appl. No.: 791,075

[22] Filed: Nov. 12, 1991

Related U.S. Application Data

[60] Division of Ser. No. 661,693, Feb. 27, 1991, which is a continuation-in-part of Ser. No. 413,240, Sep. 27, 1989.

[51] Int. Cl.⁵ .................................................... A61B 17/00
[52] U.S. Cl. ................................................................ 606/224
[58] Field of Search .................................... 606/222–227

[56] References Cited

U.S. PATENT DOCUMENTS

| 86,769 | 2/1869 | Marriott . |
| 295,612 | 3/1884 | Bailey . |
| 299,305 | 5/1884 | Weed . |
| 877,476 | 1/1908 | Bach . |
| 1,106,667 | 8/1914 | Minahan . |
| 1,250,114 | 12/1917 | Bigelow et al. . |
| 1,558,037 | 10/1925 | Morton . |
| 1,591,021 | 7/1926 | Davis . |
| 1,613,206 | 1/1927 | Souttar .................................. 606/226 |
| 1,665,216 | 4/1928 | Morton et al. . |
| 1,678,361 | 7/1928 | Shearon . |
| 1,757,129 | 5/1930 | McClure . |
| 1,960,117 | 5/1934 | Lydeard . |
| 1,981,651 | 11/1934 | Logan . |
| 2,022,234 | 11/1935 | Everett . |
| 2,240,330 | 4/1941 | Flagg et al. ............................ 606/225 |
| 2,302,986 | 11/1942 | Vollrath . |
| 2,411,079 | 11/1946 | Baule . |
| 2,802,468 | 8/1957 | Everett . |
| 2,814,296 | 11/1957 | Everett . |
| 2,910,983 | 11/1959 | Everett . |
| 2,928,395 | 3/1966 | Forbes et al. . |
| 3,311,110 | 3/1967 | Singerman et al. . |
| 3,394,704 | 7/1968 | Dery . |
| 3,416,534 | 12/1968 | Quinn . |
| 3,534,740 | 10/1970 | Thompson ............................ 606/226 |
| 3,799,169 | 3/1974 | Beroff et al. . |
| 3,835,912 | 9/1974 | Kristensen et al. . |
| 3,875,946 | 4/1975 | Duncan . |
| 3,877,570 | 4/1975 | Barry . |
| 3,880,167 | 4/1975 | Hardwick . |
| 3,890,975 | 6/1975 | McGregor . |
| 3,910,282 | 10/1975 | Messer et al. . |
| 3,918,455 | 11/1975 | Coplan .................................. 606/225 |
| 3,924,630 | 12/1975 | Walldorf . |
| 3,926,194 | 12/1975 | Greenberg et al. . |
| 3,943,933 | 3/1976 | Gertzman . |
| 3,949,756 | 4/1976 | Ace . |
| 3,963,031 | 6/1976 | Hunter .................................. 606/227 |
| 3,980,177 | 9/1976 | McGregor . |
| 3,981,307 | 9/1976 | Borysko . |
| 4,054,144 | 10/1977 | Hoffman et al. . |
| 4,072,041 | 2/1978 | Hoffman et al. . |
| 4,124,027 | 11/1978 | Boss . |
| 4,127,133 | 11/1978 | Martinez .............................. 606/227 |
| 4,169,477 | 10/1979 | Bokros . |

(List continued on next page.)

FOREIGN PATENT DOCUMENTS

0358451  3/1990  European Pat. Off. .
3223153  8/1983  Fed. Rep. of Germany .
2432861  1/1974  France .

OTHER PUBLICATIONS

Raychem Corporation Product specification RT-850 for Thermofit TM Kynar Tubing dated Mar. 6, 1984.

*Primary Examiner*—Stephen C. Pellegrino
*Assistant Examiner*—Gary Jackson
*Attorney, Agent, or Firm*—Thomas R. Bremer; Peter G. Dilworth; Rocco S. Barrese

[57] ABSTRACT

A needle-suture combination is provided. A shrinkable tubing is employed to secure the needle to the suture. The tubing shrinks in response to heat. Suture materials which are heat labile are desensitized prior to tubing attachment to preserve the integrity of the suture material. Attachment parameters may be controlled to provide standard needle attachment or removable needle attachment.

29 Claims, 7 Drawing Sheets

U.S. PATENT DOCUMENTS

| | | |
|---|---|---|
| 4,359,053 | 11/1982 | Benjamin . |
| 4,411,654 | 10/1983 | Boarini et al. . |
| 4,596,728 | 6/1986 | Yang et al. . |
| 4,624,879 | 11/1986 | Van Dirjck et al. . |
| 4,672,734 | 6/1987 | Kawada et al. . |
| 4,792,336 | 12/1988 | Hlavacek et al. . |
| 4,805,292 | 2/1989 | Noguchi . |
| 4,926,860 | 5/1990 | Stice et al. ............... 606/224 |
| 5,051,107 | 9/1991 | Korthoff ............... 606/227 |
| 5,059,212 | 10/1991 | Korthoff ............... 606/227 |
| 5,067,959 | 11/1991 | Korthoff ............... 606/227 |
| 5,084,063 | 1/1992 | Korthoff ............... 606/227 |

METHOD FOR ATTACHING A SURGICAL NEEDLE TO A SUTURE

CROSS-REFERENCE TO RELATED APPLICATION

This is a divisional of copending U.S. application Ser. No. 07/661,693 filed Feb. 27, 1991, which is a continuation-in-part of commonly assigned, copending U.S. patent application Ser. No. 07/413,240, filed Sep. 27, 1989.

BACKGROUND OF THE INVENTION

The present invention relates to a combined surgical needle-suture device, and, more particularly, to such a device in which a shrinkable tubing attaches a suture to a surgical needle.

For many years, surgeons have employed needle-suture combinations in which a suture or ligature is attached to the shank end of a needle. Such needle-suture combinations are provided for a wide variety of monofilament and braided suture materials, both absorbable and non-absorbable, e.g., catgut, silk, nylon, polyester, polypropylene, linen, cotton, and absorbable synthetic materials such as polymers and copolymers of glycolic and lactic acids.

Needle-suture combinations fall into two general classes: standard needle attachment and removable or detachable needle attachment. In the case of standard needle attachment, the suture is securely attached to the needle and is not intended to be separable therefrom, except by cutting or severing the suture. Removable needle attachment, by contrast, is such that the needle is separable from the suture in response to a force exerted by the surgeon. Minimum acceptable forces required to separate a needle from a suture (for various suture sizes) are set forth in the United States Pharmacopeia (USP). The USP prescribes minimum individual pull-out forces and minimum average pull-out forces as measured for five needle-suture combinations. The minimum pull-out forces for both standard and removable needle-suture attachment set forth in the USP are hereby incorporated by reference.

One typical method for securing a suture to a needle involves providing a cylindrical recess in the shank end of a needle and securing a suture therein. For example, U.S. Pat. No. 1,558,037 teaches the addition of a cement material to such a substantially cylindrical recess to secure the suture therein. Additional methods for bonding a suture within a needle bore are described in U.S. Pat. Nos. 2,928,395 (adhesives) and 3,394,704 (bonding agents). Alternatively, a suture may be secured within an axial bore in a needle by swaging the needle in the region of the recess. See, e.g., U.S. Pat. No. 1,250,114. Additional prior art methods for securing a suture within a needle bore include expansion of a catgut suture through the application of heat (U.S. Pat. No. 1,665,216), inclusion of protruding teeth within the axial bore to grasp an inserted suture (U.S. Pat. No. 1,678,361) and knotting the end of the suture to be inserted within the bore to secure the suture therein (U.S. Pat. No. 1,757,129).

Methods for detachably securing a suture to a needle are also well known. For example, U.S. Pat. Nos. 3,890,975 and 3,980,177 teach swaging a suture within a needle bore such that the suture has a pull out value of 3 to 26 ounces. Alternative detachable attachment methods include providing a weakened suture segment (U.S. Pat. No. 3,949,756), lubricant tipping the end of a suture to be inserted in the axial bore of a needle (U.S. Pat. No. 3,963,031), and pre-tensioning a suture that is swaged within an axial needle bore (U.S. Pat. No. 3,875,946). See also, U.S. Pat. Nos. 3,799,169; 3,880,167; 3,924,630; 3,926,194; 3,943,933; 3,981,307; 4,124,027; and 4,127,133.

Another method for attaching a suture to a needle involves the use of tubing which is secured to the shank end of the needle and to the suture. For example, U.S. Pat. No. 1,613,206 describes the use of a tubing (preferably silver) which is secured to the shank end of a needle and to a ligature. It is suggested that the tube may be attached to the needle by pressure or soldering and to the ligature by pressure or cementing. It is also suggested that the shank of the needle be of reduced cross section and that the furthest extremity of the reduced diameter shank section be provided with a spike or point upon which the suture may be secured prior to tube application.

U.S. Pat. No. 2,240,330 describes a tubing attachment method whereby the tubing and suture are releasably secured to the needle. In particular, the needle and tubing are provided with cooperating catch and abutment means which are released one from the other by rotating the needle 90° relative to the tubing (or vice versa). The tubing is manufactured from spring-tempered carbon steel or chrome nickel steel and is secured to the suture by heating the tubing and then swaging to the suture.

U.S. Pat. No. 3,311,100 relates to a flexible composite suture having a tandem linkage. The needle is secured to a flexible suture leader manufactured from a readily sterilizable plastic such as nylon, linear polyethylene, isotactic polypropylene, polyester, silk or other proteinaceous material, e.g. by inserting and crimping the leader within an axial bore in the needle shank. The opposite end of the suture leader is crimped within a connector sleeve of a thin walled metal tubing, e.g., stainless steel. The opposite end of the tubing is crimped around a stiff suture, e.g., monofilament stainless steel.

U.S. Pat. No. 3,918,455 describes a needle-suture attachment wherein a hollow suture portion is secured to the shank end of a needle which is of reduced cross-section as compared to the remainder of the needle.

Additional patents which describe the use of tubing to effect suture-needle attachment include U.S. Pat. Nos. (forming needle from U-shaped metal plate around suture), 4,359,053 (silicone tubing), 3,835,912 (laser welding of metal tube to needle), 2,814,296, 2,802,468 (chamfered tubing ends), 2,302,986, 2,240,330, 1,981,651 (needle and tubing screw threaded), 1,960,117, and 1,591,021.

Numerous disadvantages exist with methods used heretofore to effect needle-suture attachment. For example, those methods which involve the formation and use of an axial bore in the shank end of the needle require the use of expensive hole forming equipment. Moreover, it is difficult to maintain the bore concentric with the center-line of the needle and to control the depth (and diameter) of the bore when drilling the needle shank, whether using conventional drilling equipment or laser drilling. Another disadvantage is the possibility that foreign substances may inadvertently or uncontrollably be introduced into the needle bore, e.g., oil used during drilling or silicone from the needle siliconization process. Safeguards employed in an attempt to prevent the introduction of such foreign materials, e.g., water blocking during needle siliconization, are inconvenient adding time, effort and cost to the needle production process.

Attachment processes which employ bored needle shanks also limit the range of materials from which needles may be fabricated in a cost effective fashion. For example, it is exceedingly difficult to drill Series 300 stainless steel (laser drilling is required) and, once drilled, it is difficult to swage Series 300 stainless steel in a consistent and reliable manner. For this reason, Series 300 stainless steel is not employed for the vast majority of needled suture products despite its advantageous combination of strength and ductility characteristics as compared to conventionally employed Series 400 stainless steel.

Additional disadvantages associated with needle-suture attachment methods which employ bored needle shanks include the weakness imparted to the bored section of the needle, particularly after swaging, and the attendant increased possibility that the needle will fracture in this region. It is also difficult to provide a specialized surface finish to the needle shank to assist in needle attachment, e.g., a texturized surface and/or a tapered bore. Swaging equipment used in such needle-suture attachment methods is also maintenance intensive.

Needle-suture attachment methods which have employed tubings heretofore also exhibit numerous disadvantages. Methods which employ metal tubings greatly diminish the flexibility of the needle-suture combination in the attachment region. Such diminished flexibility has a deleterious effect in many surgical procedures. Swaging of the tubing to the needle and the suture is also undesirable in that swaging is time-consuming, maintenance intensive, and subject to variability in attachment force.

Moreover, needle-suture attachment methods which have employed tubings heretofore have necessarily required the use of tubing having an inner diameter essentially equal to the outer diameters of the needle shank and suture tip to be attached. Too large a difference between the aforesaid inner and outer diameters inhibits the attachment process, and prevents a tight, secure interface between needle (and/or suture) and tubing. The limited tolerance between the tubing inner diameter and the needle shank/suture outer diameters in such methods make these dimensions critical, thereby making the attachment process more difficult and time-consuming, and increasing the likelihood of attachment failure and/or rejected materials.

In an effort to overcome the aforementioned disadvantages of previously known combined surgical needle-suture devices and needle-suture attachment methods, commonly assigned, copending U.S. patent application Ser. No. 07/413,240, filed Sep. 27, 1989, the entire contents of which are incorporated herein, discloses a combined needle-suture device in which a shrinkable tubing secures a surgical needle to a suture. According to this method a heat shrinkable tubing is placed around the shank end of a needle and a suture. Energy (for example, heat at a temperature of about 175° C. or above) is applied to shrink the shrinkable tubing and bring the tubing into engagement with the needle and suture to form a combined needle-suture device.

While the use of the tubing method disclosed in U.S. patent application Ser. No. 07/413,240 for needle-suture attachment has been found to be very effective, in the case of suture materials which are heat labile (i.e., those suture materials which tend to undergo some degree of degradation upon application of energy in the form of heat thereto) it is desirable to take precautions to treat a portion of the heat labile suture to prevent the suture material which is proximate to the energy and possibly exposed to such energy during the shrinkable tubing attachment process from undergoing a degradation of its physical qualities (i.e., tensile strength, etc.) or blemishing. As used herein the term "/heat labile material" refers to materials which may undergo physical, chemical and/or biological change or breakdown when exposed to energy. A heat labile suture is a suture fabricated from a material that is heat labile and undergoes some degree of breakdown of its components when exposed to sufficient energy, for example, heat energy. Most suture materials are sensitive to energy if exposed for an extended period of time; the list of heat labile suture materials affected by heat shrinking processes includes but is not limited to catgut, silk, nylon, polyester, polypropylene, linen, cotton, and/or absorbable synthetic materials for example, copolymers of glycolic and lactic acids.

SUMMARY OF THE INVENTION

Accordingly, it is an object of the present invention to provide an improved method for attaching a shrinkable tubing to a needle and suture to provide a combined surgical needle-suture device.

It is also an object of the present invention to provide a shrinkable tubing attachment method for use with heat labile suture materials.

It is a further object of the present invention to provide an attachment method which prevents degradation of a heat labile suture material when such material is exposed to heat during shrinkable tubing attachment.

An additional object of the present invention is to provide a needle-suture attachment means which eliminates the need for drilling a bore in the needle shank and swaging a suture therein.

An additional object of the invention is to provide an attachment means which reliably secures the suture to the needle in an efficient manner, without close tolerances between elements.

An additional object is to provide a needle-suture attachment which is flexible and atraumatic.

An additional object of the invention is to provide needle-suture attachments having desired pull-out forces.

These and other objects of the invention are accomplished by a method for needle-suture attachment which involve:

a) providing a needle having a needle shank of reduced diameter;

b) placing a shrinkable tubing around the reduced diameter needle shank and a suture to be attached thereto; and, c) applying energy to the shrinkable tubing to bring the tubing into engagement with the needle shank and the suture.

In the context of this invention, the term energy as referred to in (c) above is not limited to heat energy, but may be in other forms such as for example, electric, magnetic, electromagnetic, microwave, radiation, etc.

When the suture to be attached is one fabricated from a heat labile suture material it is desirable to take steps to treat the material to prevent such material from undergoing degradation during the application of energy to effect shrinkage of the shrinkable tubing. This is generally accomplished by desensitizing the end of the suture material to be attached to protect the suture from energy related degradation.

Desensitizing the suture material may be accomplished by a wide variety of methods including but not limited to: the application of a vaporizable fluid to a tip portion of a suture such that upon exposure to energy during shrinkable tubing attachment the vaporizable fluid cools the suture material and absorbs excess energy; the application of a cryogenic fluid to a tip portion such that upon exposure to energy during shrinkable tubing attachment the tip portion of the suture is initially in a frozen condition and thus protected from the deleterious effects of the energy; and/or, directing a localized gaseous current such as, for example air, carbon dioxide, etc. to the tip portion of a suture such that upon exposure to energy during shrinkable tubing attachment the gaseous current substantially cools the tip portion and conducts energy away from the exposed suture material.

The present invention also provides a needle-suture combination in which the needle and suture are joined by a shrinkable tubing. The physical and chemical characteristics of the shrinkable tubing material, the relative diameters of the tubing, the needle shank and the suture, and the amount of energy applied to the tubing may be controlled to provide a needle-suture combination having a desired pull-out force. It is thus possible to produce standard needle-suture combinations and removable needle-suture combinations using a single attachment process and a common inventory of materials.

BRIEF DESCRIPTION OF THE DRAWINGS

The present invention will become more apparent from the following detailed description taken in conjunction with the accompanying drawings in which.

DETAILED DESCRIPTION OF PREFERRED EMBODIMENTS

The present invention relates to apparatus and methods for effecting needle-suture attachments and to such needle-suture combinations. The invention has application to any suture material, whether absorbable or nonabsorbable, natural or synthetic, braided or monofilament, and to any needle material and configuration, whether straight or curved. The invention may be used to effect standard or detachable needle attachment, as described in more detail below. The present invention has specific application to heat labile suture materials which may undergo degradation when exposed to energy.

Figure 1:
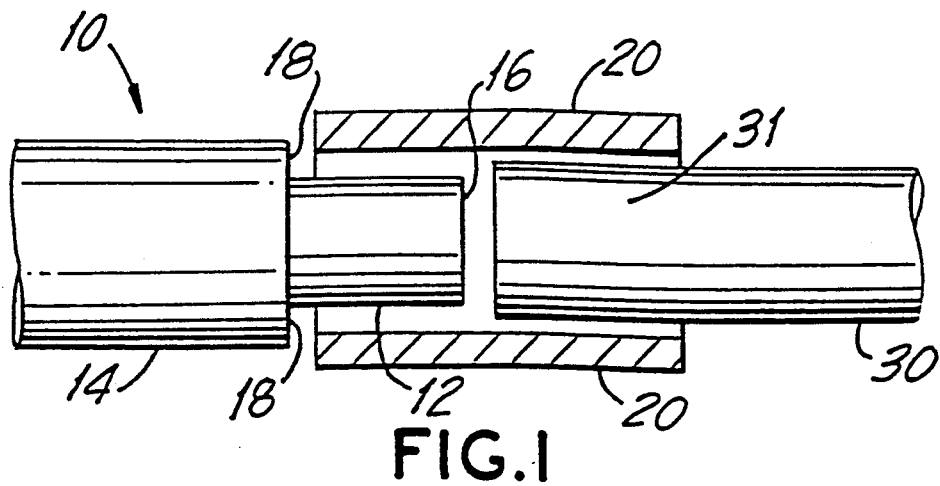
FIG. 1 is a side cross-sectional view of a needle and a suture with a shrinkable tubing positioned therearound (prior to engagement of the shrinkable tubing with the needle and suture)
Figure 2:
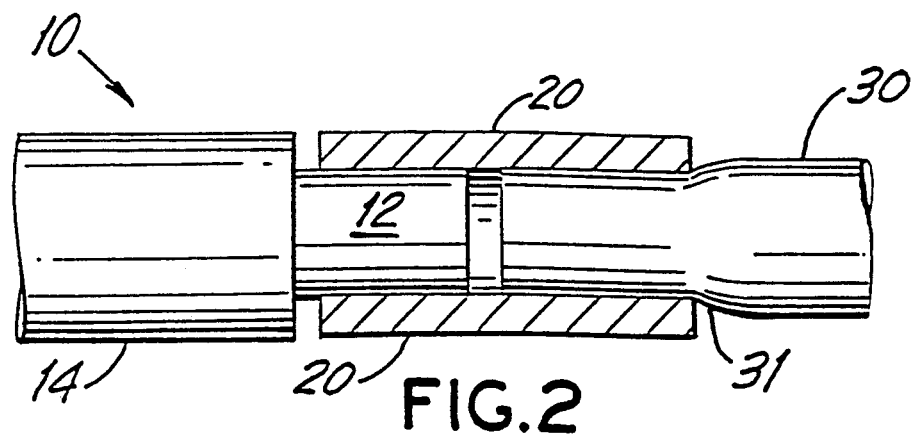
FIG. 2 is a side cross-sectional view of the tubing of FIG. 1 in engagement with the needle and suture.
Figure 3:
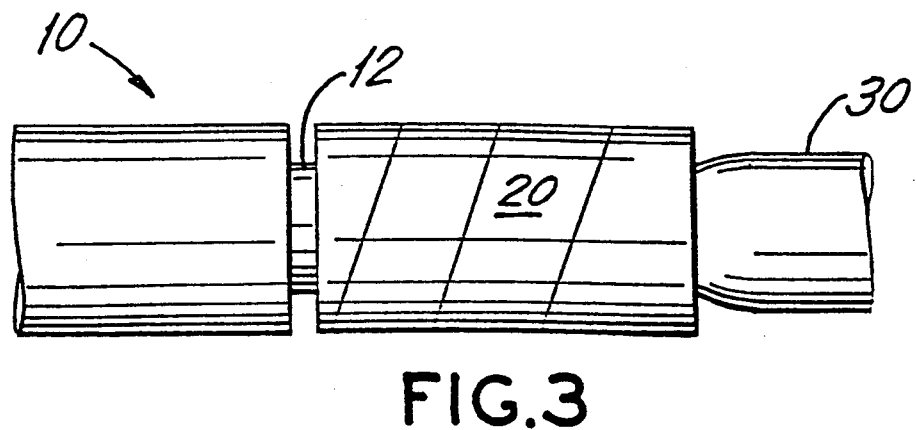
FIG. 3 is a side view of a needle-suture attachment of the present invention.
Figure 14:
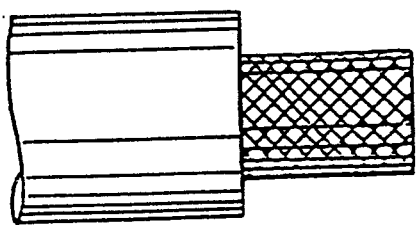
FIG. 14 is a side view of an alternative embodiment of the needle of the needle-suture attachment of the present invention in which the needle shank is scored.
Figure 16:
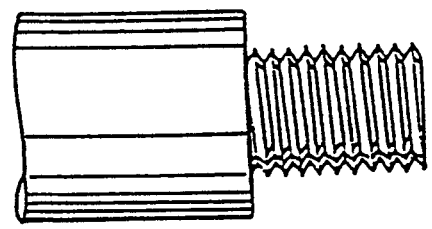
FIG. 16 is a side view of an alternative embodiment of the needle of the needle-suture attachment of the present invention in which the needle shank is threaded.
Figure 15:
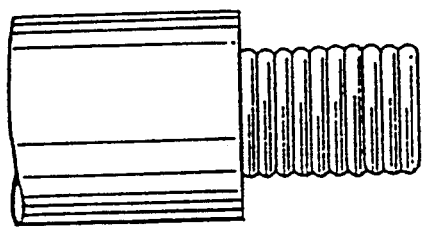
FIG. 15 is a side view of an alternative embodiment of the needle of the needle-suture attachment of the present invention in which the needle shank is ribbed.
Figure 17:
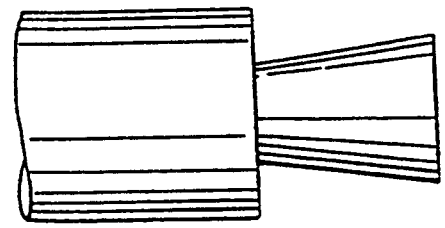
FIG. 17 is a side view of an alternative embodiment of the needle of the needle-suture attachment of the present invention in which the needle shank is tapered to expand in a direction away from a remainder of the needle.
Figure 18:
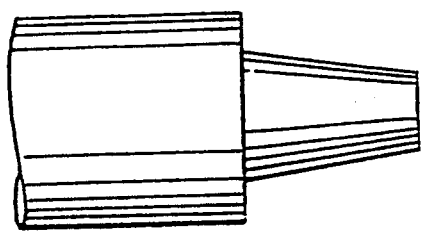
FIG. 18 is a side view of an alternative embodiment of the needle of the needle-suture attachment of the present invention in which the needle shank is tapered to expand in a direction towards the remainder of the needle.

Referring to FIGS. 1-3, needle 10 has a reduced cross-sectional diameter at its shank end 12 relative to the remainder of the needle 14. The diameter of shank end 12 may be reduced by any conventional means, e.g., machining on a lathe. Typically, shank end 12 has a diameter from 10 to 65% smaller than the remainder of the needle 14, and preferably from 25 to 50% smaller. It is also possible to provide shank end 12 with a texturized surface to facilitate gripping by shrinkable tubing 20. For example, shank end 12 may be scored, ribbed or threaded, in whole or in part (FIGS. 14-16 respectively). It may also be desirable to taper shank end 12 such that distal end 16 is of greater cross-sectional diameter than the cross-sectional diameter of shank end 12 in the region of shoulder 18, or vice versa (FIGS. 17 and 18 respectively).

Tip portion 31 of suture 30 is also positioned within shrinkable tubing 20. A gap may exist between shank end 12 and tip portion 31 (as shown in FIGS. 1 and 2) or shank end 12 may abut against tip portion 31. As shown in FIG. 1, suture 30 may initially be of uniform cross-section throughout its length. Alternatively, tip portion 31 of suture 30 may be of reduced cross-section relative to the remainder of suture 30, e.g., by tipping the suture tip with an adhesive or resinous tipping agent while suture 30 is under tension. (See, e.g., Canadian Patent No. 1,009,532 to Messores). Reducing the diameter of the suture tip as by resin tipping may be desirable to prevent brooming of the suture, particularly for multi-filament braided sutures, to rigidify the end of the suture to facilitate handling during attachment, and to allow a suture of larger diameter, e.g., a suture diameter equal to the diameter of the needle to which it is to be attached, to be more efficiently attached to the needle using the shrinkable tubing of the present invention. It is not necessary according to the present invention, however, to reduce the diameter of tip portion 31 of suture 30 to efficiently attach needle 10 to suture 30. Indeed, it may be possible or desirable to apply a tipping agent to prevent brooming without reducing suture diameter. As shown in FIG. 1, shrinkable tubing 20 initially has an inner diameter that is larger than the outer diameter of tip portion 31 of suture 30, thereby reducing the importance of suture tipping.

After shrinkable tubing 20 is placed around shank end 12 of needle 10 and tip portion 31 of suture 30, energy is applied to tubing 20. In response to this energy, tubing 20 contracts or shrinks and engages shank end 12 and tip portion 31 of suture 30. The overall length of tubing 20 may also be affected by the application of energy, e.g., the length of tubing 20 may reduce. Thus, the shrinking of tubing 20 brings the inner surface of tubing 20 into engagement with shank end 12 and suture 30, thereby securing suture 30 to needle 10. Suitable energy sources include heat (convective or conductive), radiation, microwave energy, etc.

As shown in FIGS. 1-2, shrinkable tubing 20 is simultaneously placed around both tip portion 31 of suture 30 and shank end 12 of needle 10 in one embodiment of the present invention. It is preferable, however, to sequentially secure tubing 20 to needle 10 and suture 30. Thus, in a preferred embodiment of the present invention, shrinkable tubing 20 is initially secured to shank end 12 through the localized application of energy to tubing 20 in the region surrounding shank end 12. After tubing 20 has been brought into engagement with shank end 12, tip portion 31 of suture 30 is inserted into tubing 20 and additional energy is applied thereto. Sequential shrinkage of tubing 20 makes it possible to vary the amount of energy used in securing tubing 20 to shank end 12 and tip portion 31 of suture 30, respectively, and to limit the exposure of suture 30 to energy during the attachment process. In accordance with the present invention, the heat labile suture tip 31 is desensitized prior to or contemporaneous with attachment to the needle shank 12 by tubing 20. It may also be desirable to cool suture 30 in the region outside tubing 20 to prevent any undesirable degradation thereof, especially if suture 30 is fabricated from a material which is heat labile.

Referring to FIGS. 2 and 3, the shrinkage of tubing 20 typically compresses suture 30 to some extent. This is particularly true where the suture is a braided, multifilament material having void spaces in its structure. For example, tubing 20 may compress suture 30 by as much as 30 to 35% for a braided, synthetic absorbable suture and by a minimal amount for a relatively stiff material such as a monofilament surgical gut.

Shrinkable tubing 20 may be manufactured from any material which shrinks, i.e., reduces in diameter, in response to the application of energy. Suitable materials include "memory metals", e.g., nickel-titanium mixtures, nickel-iron-titanium mixtures, or copper based materials, as are well known in the art (see, e.g., U.S. Pat. Nos. 3,759,552, 3,801,954, 4,198,081 and 4,773,680), and shrinkable plastic materials, such as polyvinylidene fluoride materials available from Raychem Corporation, Menlo Park, California, under the trade name Kynar. In the case of shrinkable plastic materials, the tubing is typically extruded such that the inner diameter is less than the final desired inner diameter, i.e., the inner diameter of the shrinkable tubing after energy application in the attachment method of the present invention. Thereafter, the extruded shrinkable tubing is expanded radially outward through radial expansion means to provide a tubing of expanded inner diameter as shown, for example, by tubing 20 in FIG. 1. Such plastic tubing is thus adapted to shrink or "recover" to its original extruded inner diameter in response to the application of a predetermined amount of energy.

The amount of energy applied to the shrinkable tubing to effect the desired attachment, i.e., diameter reduction, depends upon the chemical characteristics of the tubing material, the relative dimensions of the tubing, the treatment used to desensitize a heat labile suture, the shank end of the needle and the suture, the desired pull-out force or the needle-suture combination. For example, one polyvinylidene fluoride material available from Raychem Corporation (RT-850) shrinks at temperatures greater than 175° C., and is adapted to recover to about 50% of its radially expanded inner diameter. In such case, tubing 20 may be brought into engagement with shank end 12 of needle 10 and suture 30, either simultaneously or sequentially, by heating tubing 20 to a temperature above 175° C. Tubing 20 may be heated through contact with a hot gas stream or with heated dies, or by other heating means. Preferably the shrink tubing is attached to the needle shank by conductive heating of the needle shank, thereby heating the shrinkable tubing only in the region around the shank. Typically, the outer diameters of shank end 12 and suture 30 (in the region inserted into tubing 20) are greater than the fully recovered diameter of tubing 20, e.g., greater than 50% of the initial inner diameter of tubing 20 for the RT-850 material, such that tubing 20 engages shank end 12 and suture 30. This engagement provides the needle-suture combination of the present invention.

Machining of the needle to provide a reduced diameter needle shank is much easier and more controllable than the drilling processes, and permits the use of needle alloys which have previously been impractical, e.g., Series 300 stainless steel and MP35N (available form SPS Technologies). These heretofore impractical alloys have advantageous strength and ductility characteristics as compared to conventionally used Series 400 stainless steels. Moreover, an unreliable, expensive and maintenance intensive swaging process is replaced by a sterile, controllable and relatively inexpensive energy supply. The tubing used in the present invention may be color coded to designate suture material, standard versus detachable attachment, etc., particularly where a plastic tubing is employed.

The attachment method of the present invention is also much more efficient from a processing and inventory control standpoint. For example, the tubing may be removed from a needle and the needle attached to a fresh suture, e.g., in instances where the suture and/or attachment properties of the initial suture-needle combination are outside specifications. In many instances, the suture may also be recovered and reused, thereby greatly reducing processing waste. The range of acceptable suture diameters is greatly expanded due to the ability of the tubing to recover or shrink to varying degrees, thereby minimizing the likelihood that suture production will be rejected for inability to attach needles thereto. A single tubing size may be used to attach several needle sizes with the same shank diameter because the shrinkable tubing is capable of recovering or shrinking to varying degrees. This greatly simplifies inventory considerations.

Needle-suture combinations produced according to the present invention are atraumatic and advantageously exhibit flexibility in the attachment region. Both standard needle attachment and detachable needle attachment products may be produced with great processing ease.

As noted above, the attachment method of the present invention may be easily used to effect both standard needle attachment and detachable needle attachment. Preferably, the pull-out force of a given needle-suture combination is controlled through control of the energy source and the length of the tubing. Thus, using the identical inventories of needles, sutures and tubings, it is possible to produce either standard or detachable needle products through simple energy variations. In the case of detachable needle attachment, it is preferred that the attachment conditions be controlled such that the tubing remains secured to the needle once the suture is detached.

Where a surgical needle-suture device is formed in accordance with the afore-described attachment methods with a suture which is heat labile, precautionary measures may be taken to preserve the suture material to prevent or minimize its degradation. Such measures include desensitizing a heat labile suture material such that when energy is applied during shrinkable tubing attachment, the heat labile suture material is protected from degradation.

Accordingly, one method for desensitizing a heat labile suture material to protect it from degradation is to apply a vaporizable fluid to the tip portion of the suture sufficiently such that during the attachment of the shrinkable tubing to the needle and suture, the energy used to effect the attachment does not have a deleterious effect on the suture material (i.e., loss of tensile strength, etc.). The vaporizable fluid absorbs energy and vaporizes thereby directing excess energy away from the suture material to avoid degradation thereof. The vaporizable fluid may be reduced in temperature when applied to cool the suture material.

A primary criteria for the selection of a vaporizable fluid is that it be compatible with and not have a deleterious effect on the suture material being used. A broad range of vaporizable fluids is contemplated including water, liquid nitrogen, liquid helium, hydrocarbons such as Freon or fluorocarbons. One skilled in the art, given the known properties of the suture material to be used, will appreciate that other vaporizable fluids not deleterious to the suture material can be used.

Figure 4:
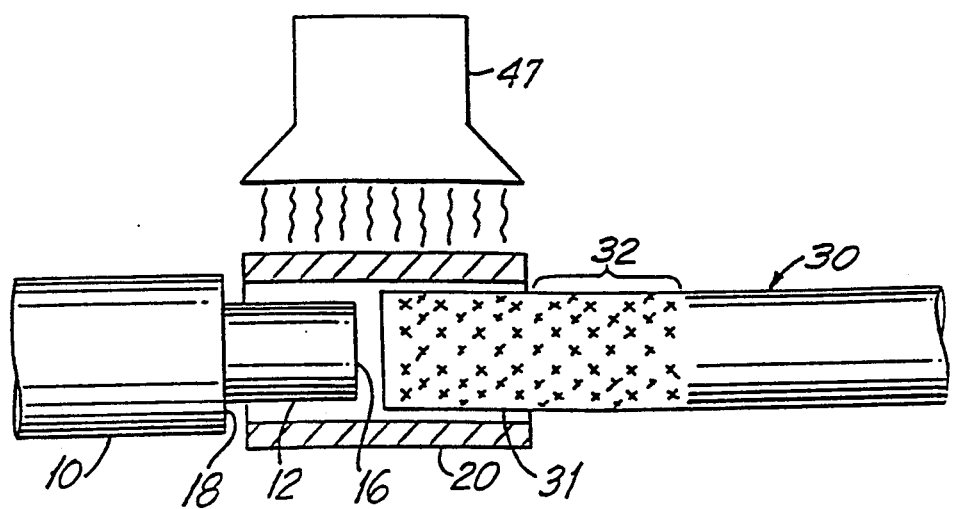
FIG. 4 is a side cross-sectional view of a needle and a desensitized heat labile suture surrounded by a shrinkable tubing according to the present invention.

Referring to FIG. 4, a desensitizing method using a vaporizable fluid to saturate a suture portion is illustrated. Tip portion 31 of suture 30 is saturated with a vaporizable fluid as indicated by the cross marks. Shrinkable tubing 20 is placed around needle shank 12 of needle 10 and tip portion 31 of suture 30. Thereafter energy is applied for example, by heat source 47 to effectuate the needle-suture attachment and provide a combined needle-suture device. Tip portion 31 which is saturated with the vaporizable fluid is unblemished due to the cooling qualities and/or vaporization of the fluid.

The amount of vaporizable fluid applied to a suture portion is a function of the suture material's sensitivity to energy, the suture's size and the heat transfer characteristics of the vaporizable fluid selected. Preferably, a portion of the suture is coated sufficiently to minimize or eliminate damage. Furthermore, in certain attachment methods to be explained herein it may also be necessary to extend the saturation to an area past the tip portion 31 of suture 30 to adequately protect this area when exposed to energy either directly or indirectly.

Figure 5:
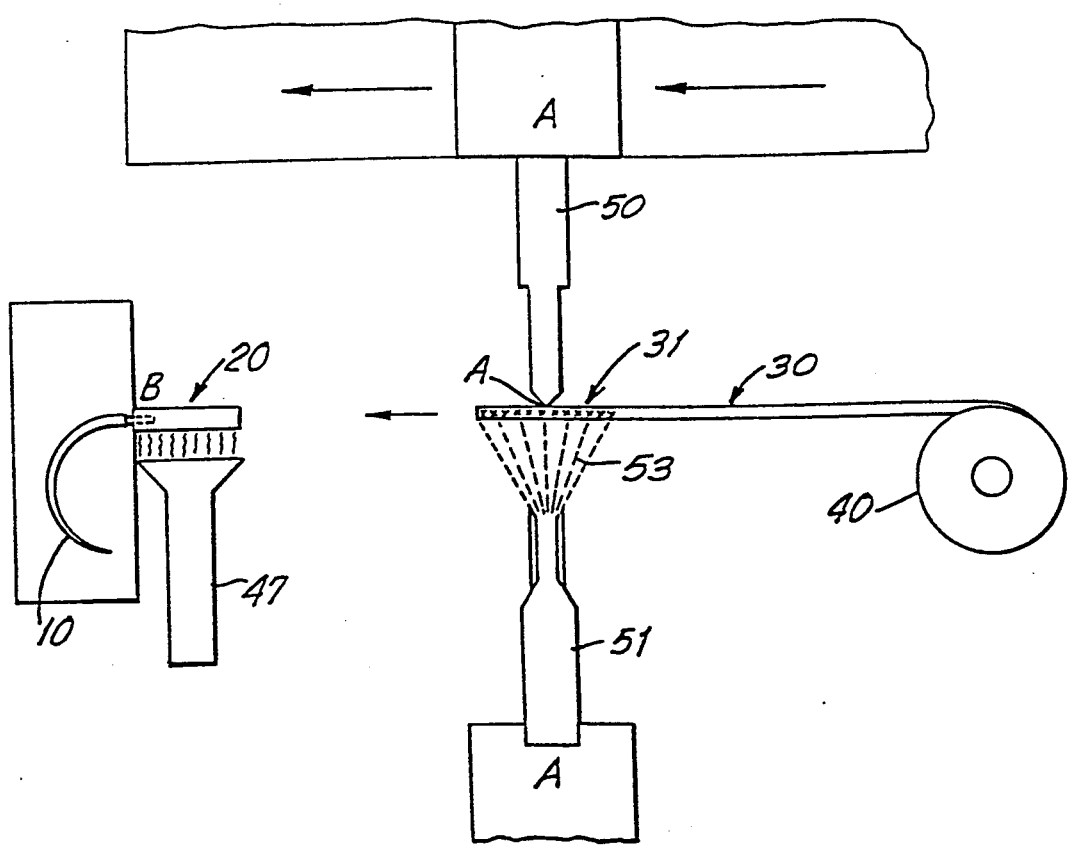
FIG. 5 is a side view of an apparatus used to apply a vaporizable fluid to a heat labile suture material prior to insertion into the shrinkable tubing.

The vaporizable fluid may be applied prior to or during the suture's exposure to energy in the attachment process. Suitable methods for the former include either brushing or spraying fluid on the suture or immersing the suture into vaporizable fluid prior to insertion into shrinkable tubing 20. Referring to FIG. 5, a mechanized spraying method for saturating tip portion 31 of suture 30 prior to exposure to energy is illustrated. Suture 30 is fed off a reel 40 of suture thread. The tip portion 31 of suture 30 is directed by retaining means 50 of linear motion device 55 which maneuvers the suture 30 towards the attachment area B. When tip portion 31 is aligned with the spraying mechanism 51 at position A, adjacent the attachment area, the spraying mechanism 51 is activated and supplies a stream of fluid 53 or mist onto tip portion 31 (as indicated by the cross marks). Thereafter the suture 30 is maneuvered towards the tubing attachment area B in which tip portion 31 is inserted into shrinkable tubing 20. The needle-suture attachment is completed by the application of energy by heat source 47 as described above. The flow of vaporizable fluid from the spraying mechanism may be adjusted for different suture sizes, absorption qualities, etc.

Figure 6:
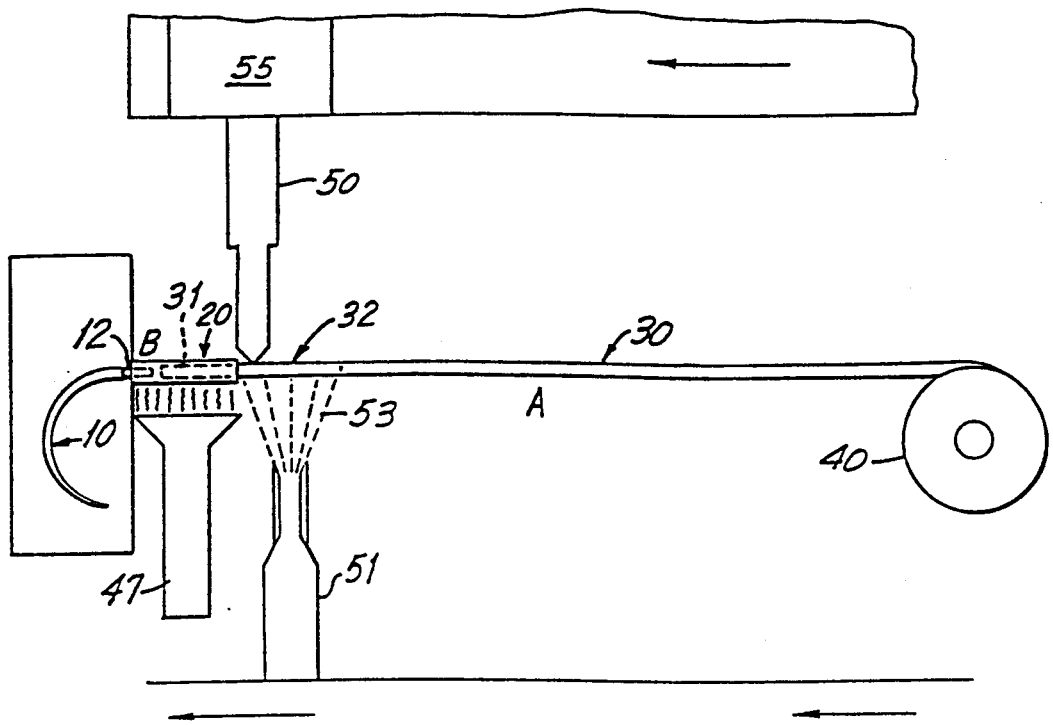
FIG. 6 is a side view of an apparatus in which a vaporizable fluid is applied to a heat labile suture material after insertion into the shrinkable tubing and simultaneous with the application of energy.

Although coating tip portion 31 prior to exposure to energy is highly effective in protecting the suture material, it is sometimes desirable to apply vaporizable fluid to tip region 31 during or simultaneous with its exposure to energy in the attachment process. Referring to FIG. 6, the spraying mechanism 51 is positioned proximate to the attachment area B. Tip portion 31 of suture 30 is inserted into shrinkable tubing 20 which is positioned over needle shank 12. Simultaneous with the application of energy, the spraying mechanism is activated and directs a stream or mist of vaporizable fluid 53 over adjacent portion 32 which is now exposed to energy, and continues until the attachment process is complete and the energy is deactivated.

The shrinkable tubing material which encloses tip portion 31 absorbs energy during the attachment and permits only minimal heat energy to communicate to the suture material of tip portion 31 Thus, it is sufficient to apply the vaporizable fluid directly to adjacent portion 32 which is exposed to heat energy.

Simultaneously attaching a needle and a suture to a shrinkable tubing wherein tip portion 31 is inserted into shrinkable tubing 20 prior to saturation of the suture portion is particularly applicable to sutures fabricated catgut. Catgut sutures, when damp or wet, exhibit a tendency to broom, thus creating difficulties in the tubing insertion process. By maintaining the portion of the suture to be inserted in a dry state, manufacturing difficulties are avoided.

A second method for desensitizing a heat labile suture material which is exposed to energy during a shrinkable tubing attachment process involves applying a cryogenic fluid, (i.e., liquid nitrogen, liquid helium, etc.) prior to the attachment process to substantially freeze the material of tip portion 31 of suture 30 thereby preventing substantial movement of the suture material at a molecular level. The cryogenic fluid is applied in much the same manner as the previously described method regarding the vaporizable fluid (i.e., immersing, brushing, and spraying) and preferably is distributed to include portions of the suture adjacent the shrinkable tubing attachment referred to as adjacent portion 32.

Figure 7:
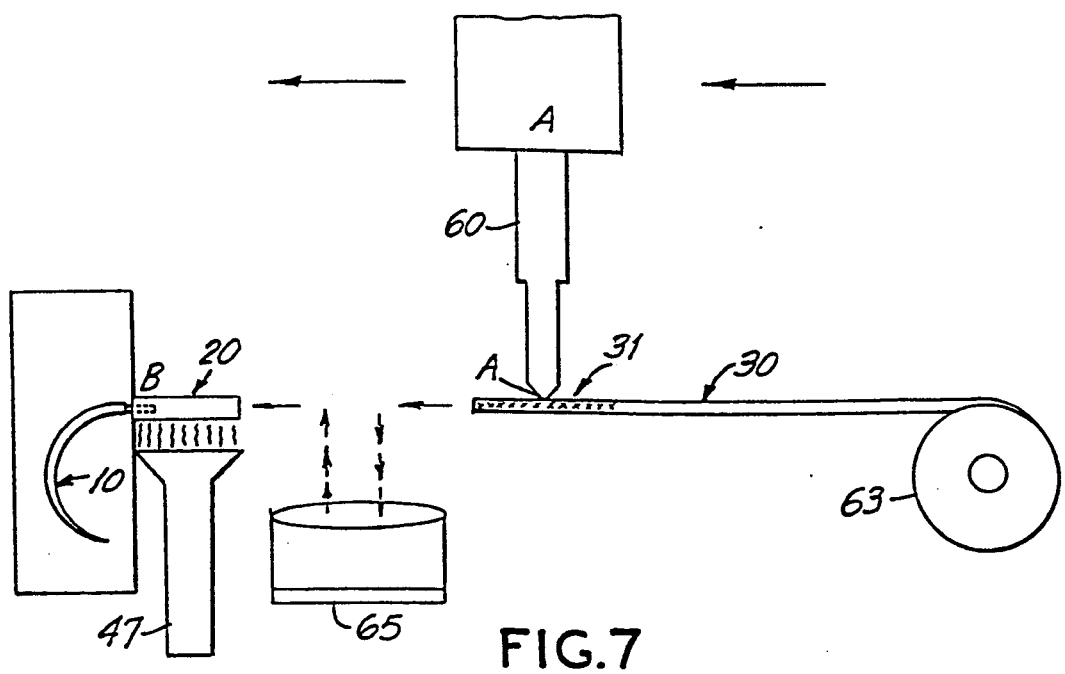
FIG. 7 is a side view of an apparatus for treating a heat labile suture material with a cryogenic fluid by FIG. 8 is a side view of an apparatus for treating a heat labile suture with cryogenic fluid by spraying prior to insertion into the shrinkable tubing.

As illustrated in FIG. 7, applying cryogenic fluids by immersing or brushing operations may be mechanized if desired to include an apparatus to carry out these functions. As shown, suture 30 is fed into an apparatus having retaining means 60 which secures tip portion 31 of suture 30. The apparatus maneuvers suture 30 towards an immersing tray 65 (as shown by the arrows) of cryogenic fluid in which tip portion 31 is immersed in the fluid and then removed. Tip portion 31, now in its frozen condition, is conveyed towards attachment area B wherein tip portion 31 is inserted into shrinkable tubing 20. Heat energy is applied to form the combined needle-suture device.

Figure 8:
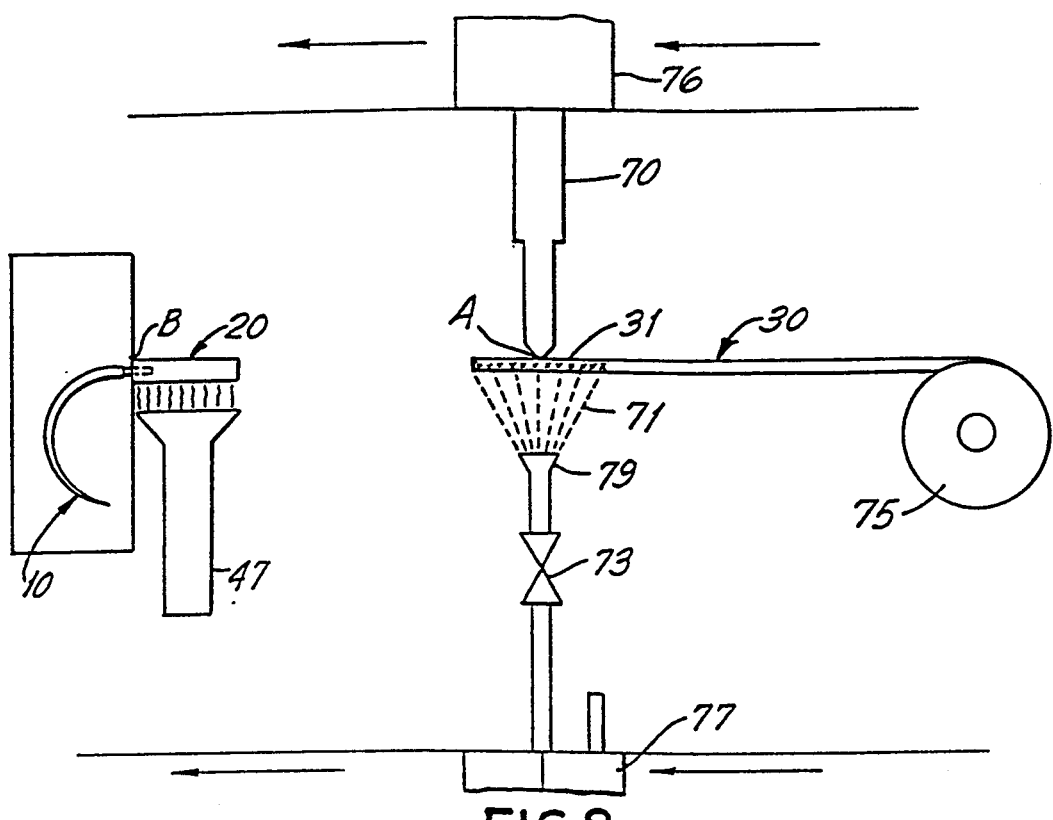

Referring to FIG. 8, cryogenic fluid may also be directed to tip portion 31 prior to the attachment process by vacuum pump apparatus 77. Discharge outlet 79 of vacuum pump apparatus 77 is positioned to direct a spray 71 of cryogenic fluid or cooling air on tip portion 31 of suture 30 immediately prior to inserting tip portion 31 into shrinkable tubing 20. As tip portion 31 is moved towards shrinkable tubing 20 in the attachment area B, the vacuum pump apparatus 77 is activated at position A wherein cryogenic fluid is released from the control valve 73 to blanket tip portion 31 including adjacent portion 32. Suture 30 is continually maneuvered by linear motion device 76 towards attachment area B wherein frozen tip portion 31 is inserted into shrinkable tubing 20. Heat energy is applied by heat source 47 to attach shrinkable tubing 20 to needle shank 12 and the tip portion 31. It is envisioned that this operation may be continuous with linear motion device 76 continuously maneuvering suture 30 directly towards the attachment area at a predetermined rate. Thus, combined needle-suture devices are manufactured at a continuous and relatively rapid rate.

Figure 9:
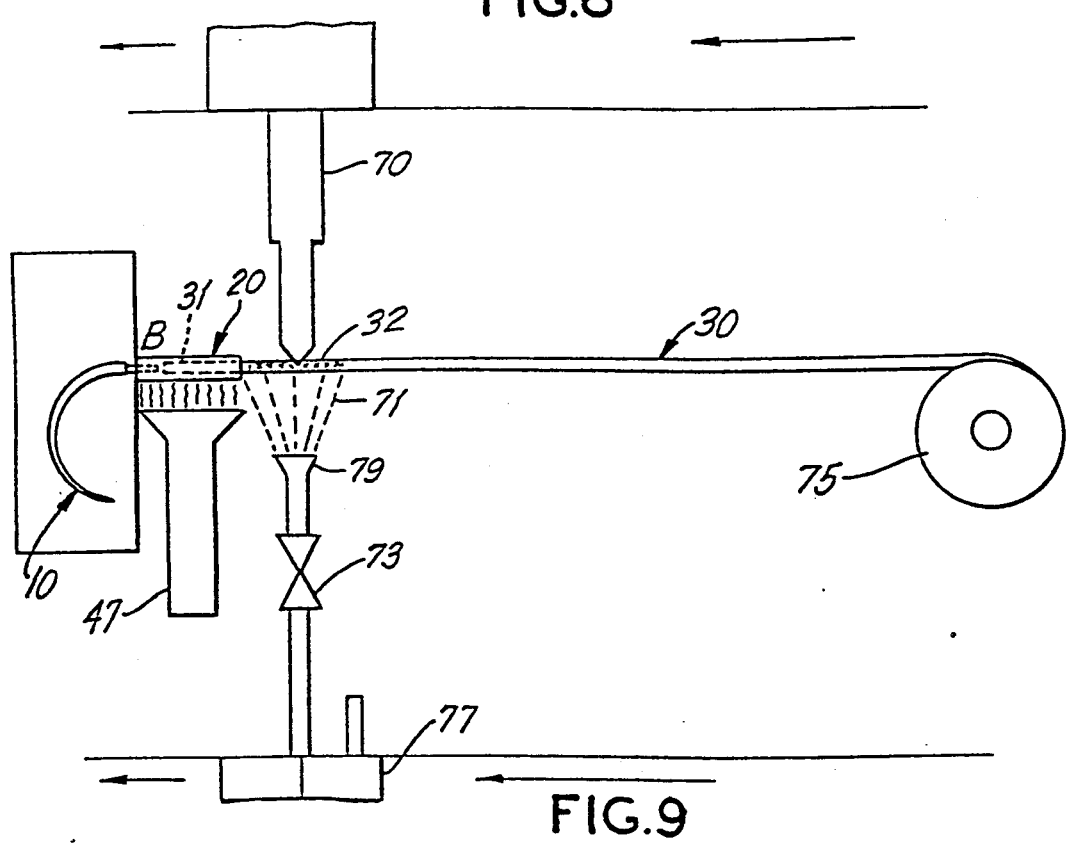
FIG. 9 is a side view of an apparatus for treating a heat labile suture material with cryogenic fluid by spraying after insertion into the shrinkable tubing and simultaneous with the application of heat energy.

FIG. 9 shows another alternative in accordance with the afore-described cryogenic vacuum pumping technique, wherein a means is provided in which cryogenic fluid may be directed at attachment area B onto a suture portion simultaneous with the application of energy during a shrinkable tubing attachment. Tip portion 31 is first inserted into shrinkable tubing 20. Subsequent to suture insertion, discharge outlet 79 of vacuum pump 77 directs a flow of cryogenic fluid or cooling air 71 over adjacent portion 32 of suture 30 while heat energy is applied by heat source 47 to effect tubing attachment. Adjacent portion 32, in a cooled condition, remains substantially unblemished while the combined needle-suture device is attached. It is contemplated that alternative cryogenic cooling arrangements, such as a "cold finger", might also be used.

Desensitizing of a heat labile suture material which is exposed to heat during a shrinkable tubing attachment process may also be accomplished by directing a gaseous current over the attachment area thus cooling the suture portion exposed to energy. The gaseous current (for example, an air current or a current of $CO_2$ may be produced by an apparatus such as, for example, a vortex air cycle. The use of gaseous currents is both economical and effective and is applicable to simultaneous and sequential needle-suture attachment methods.

Figure 10A:
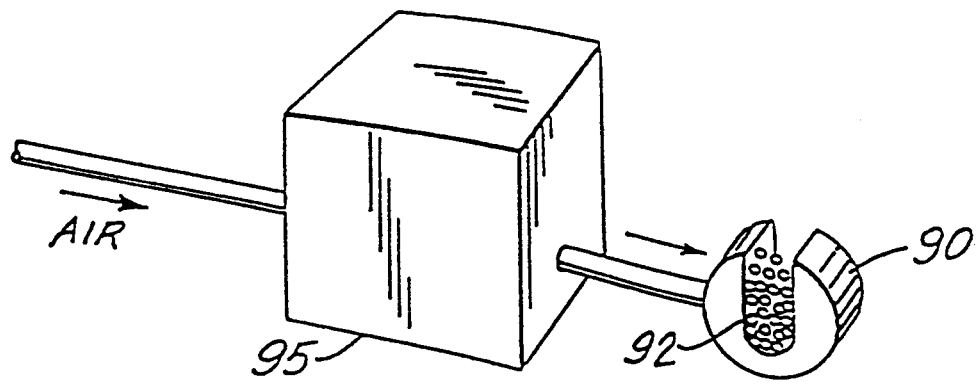
FIG. 10A is a perspective view of the cooling unit and the baffle of a vortex air cycle.
Figure 10B:
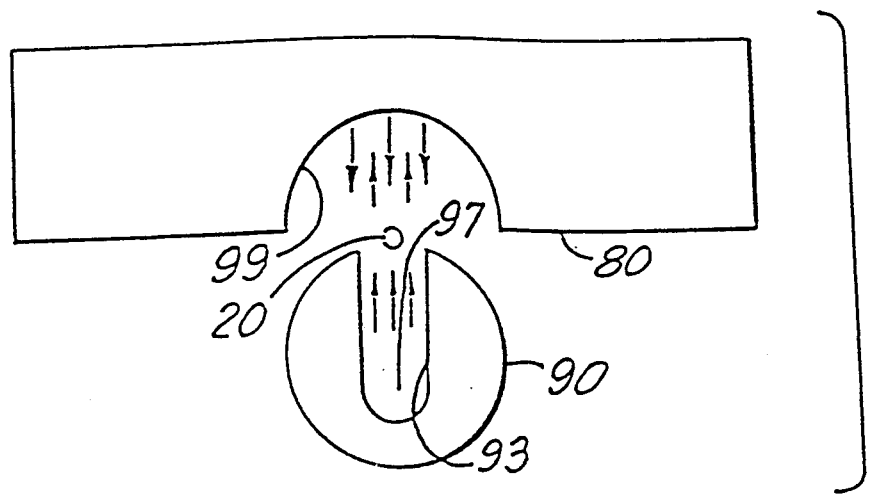
FIG. 10B is a side view illustrating the positioning of the baffle and the reflector of the vortex air cycle around the shrinkable tubing.
Figure 10C:
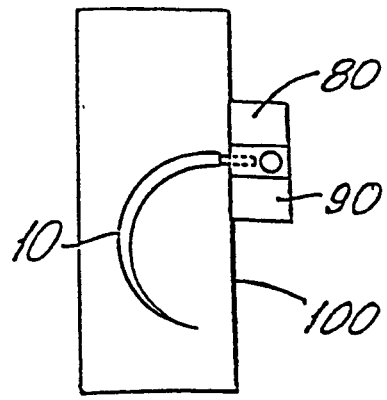
FIG. 10C is a side view of the shrinkable tubing attachment area illustrating the needle rest and the positioning of the baffle and reflector of the vortex air cycle in relation to the needle rest.
Figure 11:
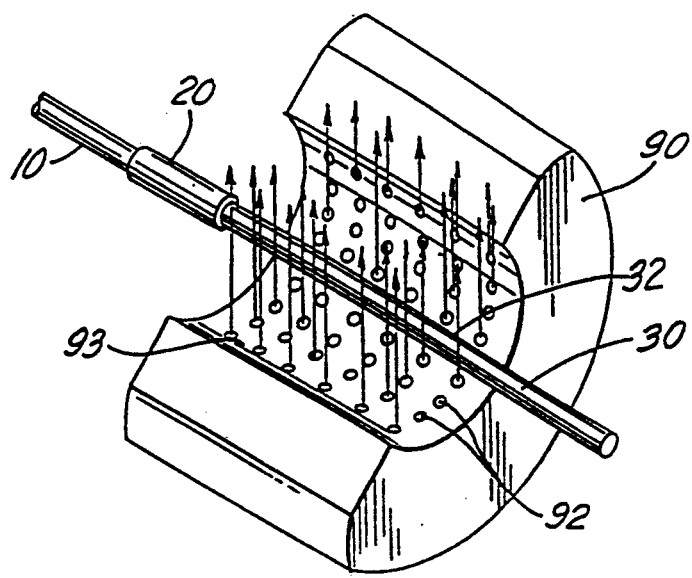
FIG. 11 is a perspective view of the baffle of the vortex air cycle of FIG. 10A illustrating the perforations of the baffle and the placement of a suture inside the baffle.

Referring to FIGS. 10A-C, the schematic illustrates an apparatus for applying a gaseous current to a suture portion, the apparatus forming a vortex cycle. The vortex cycle comprises an enclosed unit including a cooling chamber 95 (for example an industrial air conditioner) connected to a substantially U-shaped baffle 90 adapted to enclose at least a portion of the suture or a needle-suture device. U-shaped baffle 90 contains a plurality of perforations 92 on the interior surface thereof which allow cool air or gas to flow therethrough to cool a suture. Perforations 92 are dispersed throughout the inside surface 93 of the baffle to effectively cool the suture as illustrated in FIG. 11. One skilled in the art will readily appreciate that baffle 90 need not be shaped primarily like a U but may be formed in other shapes including but not limited to square, circular, rectangular, etc.

Referring again to FIGS. 10 A-C, baffle 90 includes a slot 97 which defines an inner surface 93 of baffle 90. The portion of baffle 90 containing the upper open end of the slot 97 is received within reflector 80, the slot 97 and the inner surface 99 of the reflector 80 forming an enclosure. In operation, gas is released from baffle 90 through perforations 92 and "reflected" off inner surface 99 of reflector 80. The released and reflected motion of gas from perforations 92 and inner surface 99 of reflector 80, respectively, as illustrated in FIG. 10B by the arrows, provides a "vortex" effect of gas, which in turn, establishes a curtain and an even greater disbursement of gas over the suture.

Referring to FIG. 10C, the gaseous curtain generated by the movement of the gas due to U-shaped baffle 90 and inner surface 99 of reflector 80 is situated adjacent needle rest 100 proximate the attachment area. Needle rest 100 secures a needle 10 to enable a shrinkable tubing to be inserted on the shank end of the needle prior to attachment.

Figure 12:
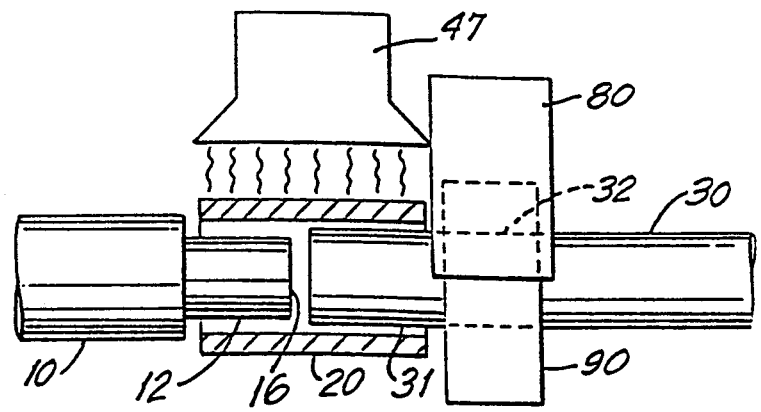
FIG. 12 is a side cross-sectional view of the positioning of the baffle and reflector of the vortex air cycle around a portion of a heat labile suture during a simultaneous attachment of the shrinkable tubing to the needle and suture.

Referring now to FIG. 12, the vortex cycle operates as follows. In a simultaneous attachment, tubing 20 is placed over shank end 12 of needle 10 and the tip portion 31 of suture 30. U-shaped baffle 90 is positioned to surround adjacent portion 32 of suture 30. Reflector 80 is positioned over the baffle 90. The vortex cycle is activated to supply an air curtain which cools the entire circumference of the adjacent portion 32. Energy is applied to shrinkable tubing 20 by heat source 47 to attach shrinkable tubing 20 and form a combined needle-suture device. The adjacent suture portion 32 remains unblemished due to the cooling effect of the air curtain generated by the baffle 90 and reflector shield 80.

The vortex air cycle may be continuous. In this case another needle is placed on the needle rest, the baffle and reflector are placed in their proper position around adjacent suture portion 32 and energy is applied to form another combined needle-suture device. The approximate cycle time for simultaneously attaching a tubing to a needle and suture ranges from 2 to 10 seconds. The air pressure generated at the baffle 90, measured at the point of disbursement (at perforations 92) ranges from about 5 to 40 psi.

It may be preferable in some instances to sequentially attach the needle and suture. Sequential attachment is a two-step process involving first the attachment of the shrinkable tubing to the needle and thereafter the attachment of the shrinkable tubing (with the attached needle) to the heat labile suture.

Figure 13:
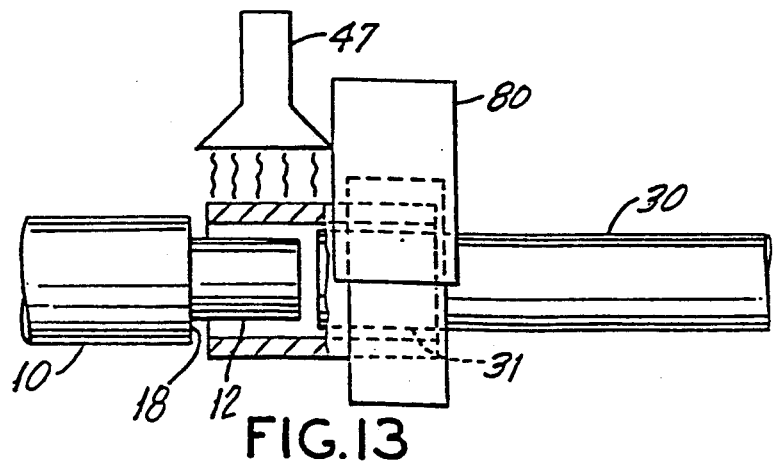
FIG. 13 is a side cross-sectional vie of the positioning of the baffle and reflector of the vortex air cycle around a portion of the shrinkable tubing during the attachment of a needle to a shrinkable tubing.

Referring to FIG. 13, the positioning of the vortex air cycle components for the attachment of shrinkable tubing 20 to needle 10, is illustrated. Specifically, U-shaped baffle 90 and reflector 80 are positioned to cover the distal portion of shrinkable tubing 20 which will be subsequently shrunk to attach suture 30 in the second step of sequential attachment. The vortex cycle is activated and an air curtain is formed inside of U-shaped baffle 90 and inner surface 99 of reflector 80. This curtain of cool air is disbursed over the distal portion of shrinkable tubing 20. When energy is applied by heat source 47 to form the needle attachment to shrinkable tubing 20, the portion of shrinkable tubing 20 enclosing needle shank 12 shrinks and forms a needle-shrinkable tubing attachment while the distal portion of shrinkable tubing 20 positioned in the air curtain and enclosed by baffle 90 and reflector shield 80 remains unblemished. The attachment parameters for this needle-shrinkable tubing attachment are air pressure of about 35 to 45 psi and preferably about 42 psi and cycle time from 1 to 20 seconds and preferably about 3 to 12 seconds.

To complete the second step of the sequential attachment and to attach suture 30 to the now existing needle-shrinkable tubing attachment, U-shaped baffle 90 and reflector 80 are positioned as illustrated in FIG. 12 over adjacent portion 32 of suture 30. Energy is applied locally to the remaining portion of the shrinkable tubing (the portion needed to attach shrinkable tubing 20 to tip portion 31) while the air curtain is generated to protect adjacent portion 32 of suture 30 to complete the attachment and form a combined needle-suture device. The attachment parameters for the suture-shrinkable tubing attachment process include an air pressure of about 35 to 45 psi and preferably about 42 psi and a cycle time ranging from about 1 to 20 seconds and preferably about 2 to 10 seconds.

For both stages of the attachment, the temperature of the air released by the air conditioner and entering the baffle to cool the suture ranges in value from about 100±5° to 280±5° F.

The vortex air cycle is a desirable method for attachment because it is relatively inexpensive and is well-suited for sequential as well as simultaneous needle-suture attachment. In accordance with the first step of a sequential needle-suture attachment (attaching a needle to a shrinkable tubing) a whole inventory of needle-shrinkable tubing attachments can be manufactured at one time and then subsequently the suture attachment can be completed at a later date thereby facilitating inventory control. Additionally, the vortex air cycle is a clean operation.

The needle-suture attachment method of the present invention has many advantages over previous attachment methods. Desensitizing a heat labile suture material according to one of the afore-described methods herein will preserve the integrity of the material as well as the physical characteristics (i.e., tensile strength) and will provide a combined needle-suture device which is unblemished, flexible, and inexpensive to manufacture.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A needle-heat labile suture attachment comprising:
   (a) a needle having a shank of reduced cross-section;
   (b) a heat labile suture having a desensitized tip portion; and
   (c) a shrinkable tubing around said needle shank and said desensitized tip portion of said heat labile suture.

2. The needle-heat labile suture combination of claim 1 wherein the heat labile suture is fabricated from a nonabsorbable heat labile material selected from the group consisting of silk, nylon, polyester, polypropylene, linen and cotton.

3. The needle-heat labile suture combination of claim 1 wherein the heat labile suture is fabricated from an absorbable heat labile material selected from the group consisting of catgut and synthetic materials including polymers and copolymers of glycolic and lactic acids.

4. The needle-heat labile suture attachment of claim 1, wherein said needle is detachably secured to said suture. proximate said shank end of said needle.

5. The needle-heat labile suture attachment of claim 1, wherein said shank of said surgical needle has a diameter from 10 to 65% smaller than the remainder of the needle.

6. The needle-heat labile suture attachment of claim 1, wherein said shank of said surgical needle has a diameter from 25 to 50% smaller than the remainder of the needle.

7. The needle-heat labile suture attachment of claim 1, wherein said shank is ribbed, scored and/or tapered in whole or in part.

8. The needle-heat labile suture attachment of claim 7, wherein said shank increases in diameter towards a distal end of said shank.

9. The needle-heat labile suture attachment of claim 1, wherein said shank and said tip portion of said suture abut within said shrinkable tubing.

10. The needle-heat labile suture attachment of claim 9, wherein said shank tapers in diameter towards a distal end of said shank.

11. The needle-heat labile suture attachment of claim 1, wherein said shank has a texturized surface.

12. The needle-heat labile suture attachment of claim 1, wherein said needle is straight.

13. The needle-heat labile suture attachment of claim 1, wherein said needle is manufactured from a material selected from the group consisting of Series 300 stainless steels, Series 400 stainless steels and MP35N.

14. The needle-heat labile suture attachment of claim 1, wherein said tip portion of said suture is coated with a liquid selected from the group consisting of adhesives and resins.

15. The needle-heat labile suture attachment of claim 14, wherein said coated tip portion of said suture is of reduced cross-section relative to the remainder of the suture.

16. The needle-heat labile suture attachment of claim 1, wherein said shrinkable tubing is manufactured from a memory metal or a shrinkable plastic material.

17. The needle-heat labile suture attachment of claim 16, wherein said needle-heat labile suture attachment is flexible in the region of said shrinkable tubing.

18. The needle-heat labile suture attachment of claim 16, wherein said tubing is color-coded to designate specific suture material.

19. The needle-heat labile suture attachment of claim 16, wherein said tubing is color-coded to designate standard or non-detachable versus detachable attachment.

20. The needle-heat labile suture attachment of claim 16, wherein said memory metal is selected from the group consisting of nickel-titanium mixtures, nickel-iron-titanium mixtures and copper based materials.

21. The needle-heat labile suture attachment of claim 16, wherein said shrinkable plastic material is a polyvinylidene fluoride material.

22. The needle-heat labile suture attachment of claim 1, wherein said shrinkable tubing compresses said tip portion of said suture.

23. The needle-heat labile suture attachment of claim 22, wherein said tubing compresses said tip portion of said suture by as much as 50% of the diameter of said suture.

24. The needle-heat labile suture attachment of claim 3, wherein said suture is a braided, multifilament.

25. A needle-heat labile suture attachment, comprising:
   a needle having a shank of reduced cross section;
   a braided, multifilament, heat labile suture having a desensitized portion; and
   a shrinkable tubing around said needle shank and said desensitized tip portion of said heat labile suture.

26. The needle-heat labile suture attachment of claim 25, wherein said braided suture is an absorbable material selected from the group consisting of catgut and synthetic materials including polymers and copolymers of glycolic and lactic acids.

27. The needle-heat labile suture attachment of claim 25, wherein said braided suture is a non-absorbable material selected from the group consisting of silk, nylon, polyester, polypropylene, linen and cotton.

28. The needle-heat labile suture attachment of claim 25, wherein said shrinkable tubing compresses said braided suture.

29. The needle-heat labile suture attachment of claim 28, wherein said shrinkable tubing compresses a braided, synthetic, absorbable suture by as much as 30 to 35%.

* * * * *